United States Patent [19]

Morton et al.

[11] 4,180,831

[45] Dec. 25, 1979

[54] IMAGE ANALYSIS DATA EXTRACTION

[75] Inventors: Roger R. A. Morton, Penfield; Cornelius J. D. McCarthy, Fairport, both of N.Y.

[73] Assignee: Bausch & Lomb Incorporated, Rochester, N.Y.

[21] Appl. No.: 821,368

[22] Filed: Aug. 3, 1977

Related U.S. Application Data

[62] Division of Ser. No. 580,392, May 23, 1975, Pat. No. 4,115,804.

[51] Int. Cl.² .............................................. H04N 5/14
[52] U.S. Cl. ..................................... 358/160; 358/93
[58] Field of Search ................. 358/107, 93, 106, 160, 358/180, 181, 183, 185; 340/324 AD

[56] References Cited

U.S. PATENT DOCUMENTS

| | | | |
|---|---|---|---|
| 3,742,125 | 6/1973 | Siegel | 358/180 |
| 3,832,485 | 8/1974 | Pieters | 358/183 |

*Primary Examiner*—Richard Murray
*Attorney, Agent, or Firm*—Frank C. Parker; Bernard D. Bogdon

[57] ABSTRACT

Techniques are disclosed for extracting measurement data from single or multiple fields of scan. Techniques are disclosed for obtaining alignment of data extracted from different fields of scan of the same image and for performing multiple fields of scan to extract data. Communication and control means are disclosed to permit the selection of a wide range of measurements using a keyboard and for the rapid presentation of data on a cathode ray tube display.

2 Claims, 8 Drawing Figures

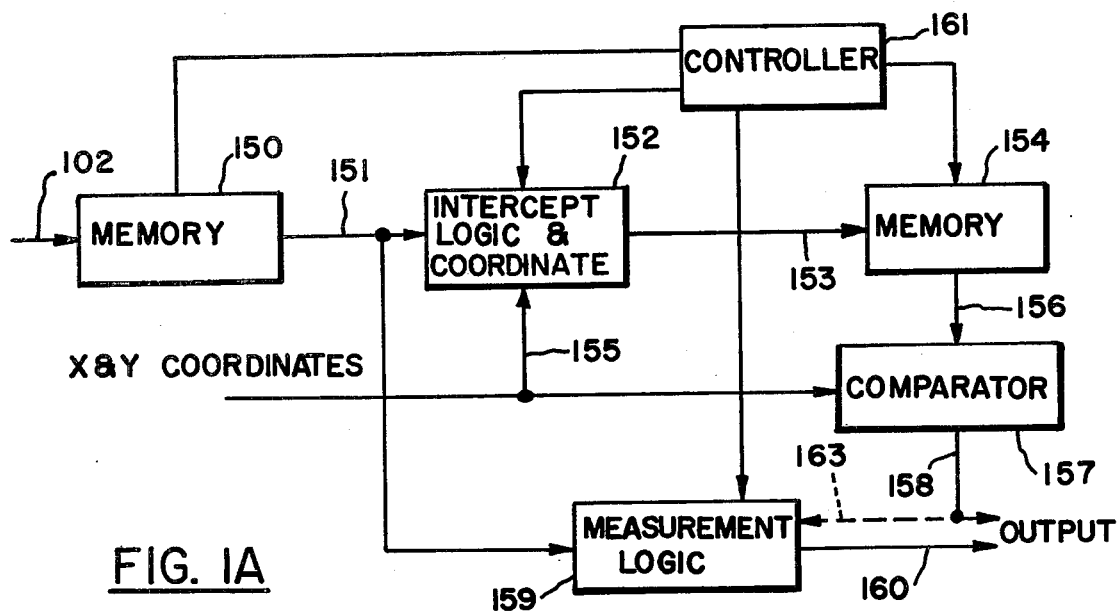
FIG. 1A
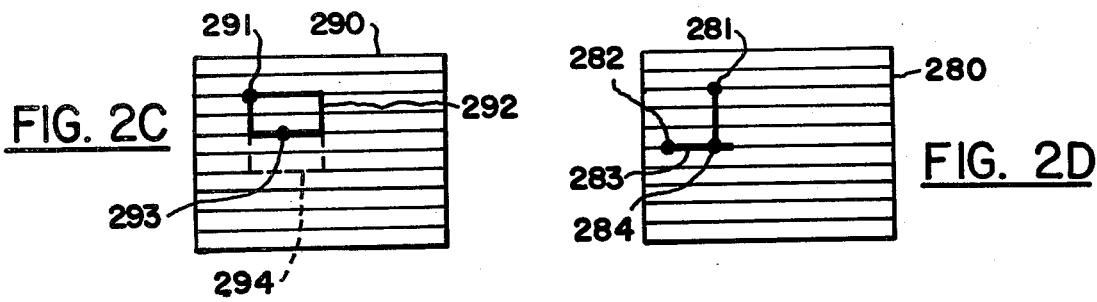
FIG. 2C
FIG. 2D
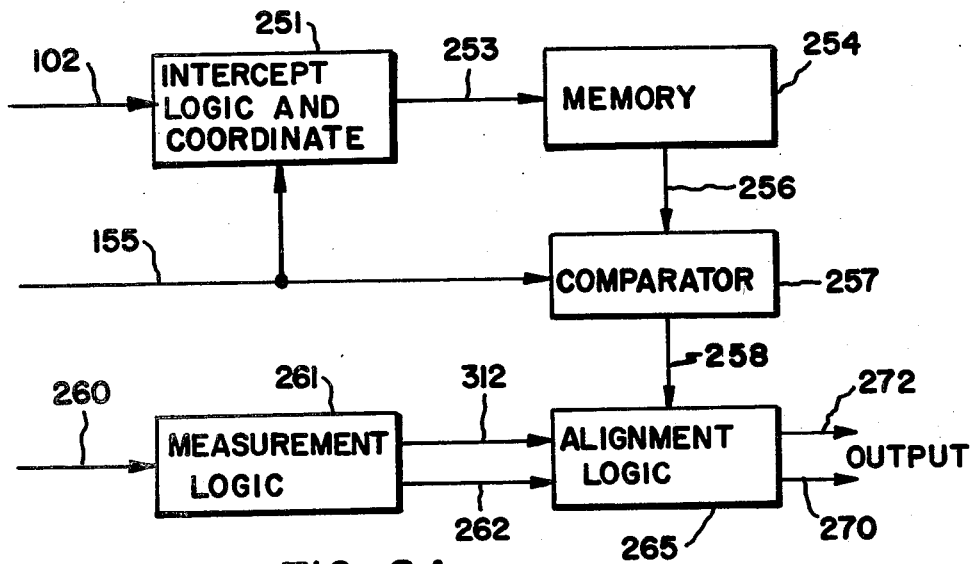
FIG. 2A

IMAGE ANALYSIS DATA EXTRACTION

This is a division, of application Ser. No. 580,392, filed May 23, 1975, which issued as U.S. Pat. No. 4,115,804 on Sept. 19, 1978.

FIELD OF THE INVENTION

This invention relates to image analysis for identifying measurement data and specifically to image analysis for extracting measurement data from single and multiple fields of scan and for the control of feature measurement generation through the use of keyboard and visual displays.

CROSS-REFERENCE TO RELATED APPLICATIONS

This application is cross referenced to and supported by concurrently filed and copending patent applications and now U.S. patents entitled (a) Image Analysis Data Transfer, U.S. Pat. No. 4,115,806, Ser. No. 580,438 for inventor R. R. A. Morton; (b) Image Analysis Measurement Apparatus and Methods, U.S. Pat. No. 4,115,803, Ser. No. 580,439 for inventor R. R. A. Morton; and (c) Image Analysis Indexing Apparatus and Methods, U.S. Pat. No. 4,115,805, Ser. No. 580,393 for inventor R. R. A. Morton.

BACKGROUND OF THE INVENTION

In performing image analysis over successive fields of view as disclosed in concurrently filed application, entitled Image Analysis Data Transfer, it is often necessary to identify from successive fields of view a specific point related to a feature or object boundary. However, the video signal which defines the feature boundary always contains a small amount of noise and thus points identified in an initial field of scan will not be exactly coincident with points identified using similar criteria on subsequent fields of scan. There will inevitably be a small amount of noise which will displace these points from field to field.

In the copending application, entitled Image Analysis Data Transfer, coordinate data from an initial field of view is stored in a memory to identify points of interest termed index points at which data is to be extracted at subsequent fields of view. These index points can define a position based, at least in part, on information derived from the video signal or a scanner for a television camera as a component of the image analysis system. A description of the function of a television camera in an image analysis system, together with a derivation of data relating to the positions of boundaries, is found in U.S. Pat. No. 3,763,357, entitled "THRESHOLD CIRCUIT FOR CONVERTING A VIDEO SIGNAL TO A BINARY VIDEO SIGNAL," issued Oct. 2, 1973 for inventor Roger R. A. Morton.

In successive fields of scan, electronic measurement logic performs calculations on the video signal and extracts data which was sampled when the scan format was in a position related to the points identified in the initial field of scan. Because of the nature of this extraction in a noise-free system, the synchronism between the coordinates of the stored points and computation of data is inherent in the designed system. However, the addition of noise which will often arise from the video signal due to the action of the television camera preamplifier which injects noise into the initially minute video signal and results in the intercept boundaries, defined in an initial field of scan, falling into a position which differ, possibly significantly, from subsequent fields of scan.

SUMMARY OF THE INVENTION

The purpose of the present invention is to overcome the effects of the noise variability in obtaining alignment between points between different fields of scan and therefore successful correlation of information obtained from successive fields of scan.

Techniques to overcome this problem are as follows. An Entire Field Memory Technique removes the noise component of the signal by storing a signal related to the image of an entire field. The related signal is then available for processing as independent scans and the repeatability provided by the memory assures scan to scan stability. For a Reference Area Technique the coordinates of the index points are stored in a memory in an initial scan. On subsequent scans the coordinate information is used to generate an enabling signal during a portion of the scan corresponding to a rectangle position with respect to the original coordinates. Information generated during this the occurrence of the enabling signal is identified as corresponding to the original coordinates. For a Reference Slice Technique, the coordinates of index points are stored in a memory in an initial scan. The coordinate information is used to generate an enabling signal of fixed duration at a time during the scan, displaced from the original index point positions. Information generated by the measuring process is placed in a memory. At each line the enabling signal is tested. When coincidence between the measurement information and the enabling signal occurs the measurement information is released from the memory, and is identified as corresponding to the original index point.

It will be readily appreciated that the apparatus described herein and in copending applications entitled, Image Analysis Data Transfer, Image Analysis Measurement Apparatus and Methods and Image Analysis Indexing Apparatus and Methods are capable of performing many different types of measurements. In addition, measurements may be performed in arbitrary sequences and measurements termed compound measurements may be derived from basic measurements. Furthermore, the selection of data may be modified by qualifying the index points as indicated in the copending application entitled, Image Analysis Data Transfer. This qualification operation, which may be based on numerous criteria falling into two primary groups, namely criteria based on coordinates and criteria based on measurements, provides a wide flexibility in the combinations of measurements which can be performed, the types of qualifications which can be performed and in subsequent selection and measurement based on these qualifications. The flexibility of these apparatus, coupled with their rapid speed of processing requires that new operator interface techniques be applied to enable the operator to control the system, to take full advantage of its flexibility, and also to present to the operator in an efficient manner, the rapidly generated data. For these reasons, further aspects of the invention disclosed herein involve the use of a special purpose keyboard to enable the operator to control both flexibly and rapidly, the operations of the system. Furthermore, in order to accommodate the basic flexibility of configuration of the apparatus, a status matrix is used whereby certain keys within the keyboard may be assigned different functions, depending on the particular aspect of the operation of the system which is being programmed. In addition, this status matrix may be modified depending on the specific configuration of the system so that the functions of certain keys may be changed or expanded as the configuration of the system is changed or expanded.

The data generated from the keyboard by the keystroke operations of the operator are passed to keyboard encoder logic which processes each keyboard stroke to generate control pulses to the functional block of the apparatus which is to implement the function requested by the keyboard stroke. Keys on the special purpose keyboard are divided into groups. One group is the group termed trigger keys. These keys initiate the operation and define the type of commands which are to follow after a given key is pressed. A further group of keys is termed functional group. These keys define the specific functions to be performed and they take on a different significance depending on the trigger key previously pressed.

The meaning of the functional keys, at any instant, determined by the trigger keys, is indicated in the status matrix which comprises a series of columns in alignment with the functional keys such that one of these columns may be illuminated using backlighting and the entries within this column indicate the meaning of the functional keys. Pressing specific trigger keys will cause one of the columns or portion thereof in the status matrix to light and therefore assign the function specified in that column to the functional keys. Examples of functional columns include the measurement column, wherein measurements such as perimeter, projected length, breadth, longest dimension, area, and so on, are assigned on a basis of one for each functional key. A further column termed the processing column specifies functional processes such as size distributions, lists of measurements, and so on. Not all functional keys need be assigned in a specific column. It will be appreciated that in such a system, other groups of keys may also be included, including numerical keys, mathematic operator keys, logical keys, and so on. Combinations of these keys permit the specification of compound measurements.

Another aspect of this invention involves the inclusion of an alphanumeric display to indicate the specific key last pressed so that the operator may observe the instructions passed through the keyboard by typing the keys appearing on the display. Another function of the alphanumeric display is to rapidly display measurements and measurement data as it is extracted. A final aspect of the display is provision for inclusion of a light pen which light pen may be used to modify the qualification of index points discussed in copending application entitled, Image Analysis Data Transfer, or may be used as will be discussed in this application for defining the position of index points.

Prior methods of controlling image analysis systems have generally used control panels containing switches and variable controls sometimes in conjunction with path panel wiring to implement the specific sequence of events required by the operator. These techniques, if applied into the apparatus and described herein and in the copending applications will tend to limit the overall capability of the system because of the inherent inflexibility of any front panel combination of knobs, wherein the only operations available are already specified by the combinations of knob positions. In a special purpose keyboard on the other hand, a very large number of different sequences of keystroke combinations may be performed and in a keyboard having, for example, 40 or more keys, the number of controlling combinations which can be communicated through the keyboard is far larger than is available with front panel knobs or patch panels. Thus, the special keyboard approach thereby provides greater flexibility of control than was available in prior systems. Furthermore, the special purpose keyboard in combination with the status matrix greatly reduces the training required for new operators, compared, for example, with a general purpose keyboard, such as a typewriter keyboard. A further aspect that simplifies operation is the alphanumeric display and its facility for indicating when the operator has pressed an erroneous key sequence.

BRIEF DESCRIPTION OF THE DRAWINGS

FIG. 1A illustrates an image analysis system for storing a video signal and generating data from the stored signal according to the principles of the disclosed invention.

FIG. 2A illustrates an image analysis system for extracting and aligning data.

FIG. 2C shows an index and data transfer point with respect to FIG. 2B.

FIG. 2D shows an index and data transfer point with respect to FIG. 3.

DETAILED DESCRIPTION OF THE PREFERRED EMBODIMENT

Figure 1B:
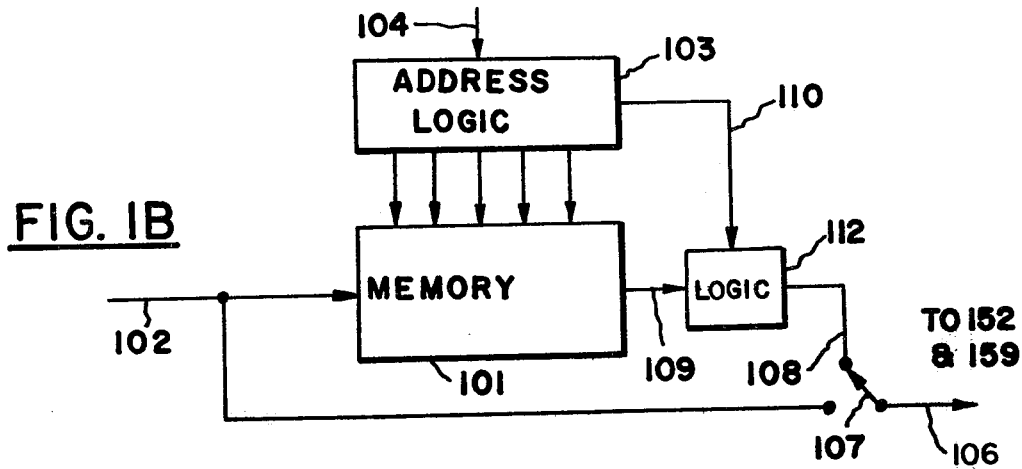
FIG. 1B illustrates a memory for storing the video signal of FIG. 1A.

The entire field memory technique for establishing alignment between points on successive scans ensures that there is no difference between video signals of different fields of scan, by storing video signals from the initial field of scan digitally in a memory, such as memory 108 of FIG. 1A of U.S. Pat. No. 4,115,806, entitled Image Analysis Data Transfer. FIG. 1A hereof illustrates an overall block diagram of the signal paths associated with this invention which are in part an abbreviated version of those disclosed in FIG. 1A of copending application entitled Image Analysis Data Transfer. Intercept information enters on line 102. Such information may, for example, be pulses corresponding to the boundaries of features to be measured or it may correspond to the actual video signal, or, alternatively, it may comprise a number of signals identifying boundaries of objects having different gray values which are to be measured. The signal on line 102 enters the memory 150, which simultaneously with storing the signal, will output the signal on line 151. The memory 150 accommodates the video signal information on line 102 for an entire scan of the field of view, and stores this video signal information in such a manner that it is reproduceable subsequently on line 151 in a form similar to that originally occurring. The output reproduction rate from memory 150 need not correspond to the original scan rate at which the video signal was generated from the field of scan and stored. If the output rate does not correspond to the original rate of generation, subsequent references to field of scan, in describing this technique, refer to the conceptual field of scan implied in the output rate of the reproduced video signal from memory 150. The specific configuration of memory 150 will be described in more detail with respect to FIG. 1B.

On a first field of scan, the video signal or a signal related thereto is stored in memory 150 and also, but not necessarily, on the first scan the intercept logic control and X coordinate circuitry 152 identifies specific index points of the signal on line 151 in a manner similar to that described with particular reference to the initial field of scan discussion relative to FIG. 1A in the concurrently filed application entitled Image Analysis Data Transfer. Index points are defined as points which, for example, may be the leading and/or trailing edges of features at scan intercepts, as represented by the generated video signals, or the topological points of a feature or, alternatively, topological points of a feature or intercept points selected with regard to a specific line or a specific spacing relating to the coordinates of index points selected to ensure that the index points are not being spaced too close to each other. The occurrence of these index points is determined by the intercept logic and coordinate circuitry 152. The information is passed on line 153 to a memory 154 to store the specific coordinates of the index points. The intercept logic 152 places coordinate data on line 153, by strobing by an AND gate in intercept logic 152, the X and Y coordinates presented on line 155. The X and Y coordinates on line 155 are generated by means of X and Y counters, counting in synchronism with a scan video signal being outputed from memory 150 at the time the index point is determined to occur within the intercept logic 152.

During a subsequent measurement field of scan, memory 154 outputs stored X and Y coordinate information on line 156 into a comparator 157, which compares the X and Y coordinate information on line 156 with current X and Y coordinates presented on line 155. When equality is sensed, comparator 157 generates a an index pulse on line 158. In addition, memory 150, during the measurement field of scan, reproduces the video signal on line 151 corresponding to the previously stored signal and, hence, corresponding to the data initially passed on line 151 during the scan in which memory 154 was loaded. This data is read through line 151 to measurement logic 159 which extracts a desired measurement from the signal presented on line 151 using the techniques disclosed in the beforementioned concurrently filed patent applications. Measurement logic 121 of FIG. 1A and the alternative measurement logic of FIG. 4B of U.S. Pat. No. 4,115,806, entitled Image Analysis Data Transfer are illustrative of such systems.

At the time of extraction or a small time thereafter the results of the extraction process are outputed on line 160. Thus, on line 160 data is presented which is synchronous with the data on line 158. The data on line 158 describes the occurrence of index points as stored in memory 154, and measurement logic 159 outputs data at a variety of points as described in concurrently filed application entitled, Image Analysis Data Transfer, now U.S. Pat. No. 4,115,806, with specific reference to comparator 126 and measurement logic 121 thereof at FIG. 1A. Because the data passing on line 151 is identical in each field of scan by virtue of it being reproduced from memory 150, variations from field to field are avoided and coincidence is assured between index pulses occurring on line 158 and measurement data passing on line 160.

The function of controller 161 is to coordinate the operations of the blocks described, for example, by coordinating the read periods and write periods of memories 150 and 154 and controlling the intercept logic and coordinate function 152 and measurement logic 159.

An alternative embodiment of this circuitry permits the pulse in line 158 to pass along dotted line 163 to measurement logic 159 to cause the measurement logic to release the data on occurrence of a pulse on line 158.

Yet another alternative embodiment is to use the intercept control logic and X coordinate block 152 and the measurement logic 159 to share common electronic hardware. These could perform the functions already described for intercept logic 102 and measurement logic 121 at FIG. 1A in the beforementioned concurrently filed patent applications, using common hardware to take advantage of the similarities of function. Detailed examples of the implementation of each of these blocks are outlined in the referred to application, now U.S. Pat. No. 4,115,806, entitled Image Analysis Data Transfer, specifically, for example, with reference to FIGS. 2D, 4A and 4B. Because both of these blocks, 152 and 159, output data in the form of X and Y coordinates or information related thereto, it is practical to affect an economy of components by ensuring that operations requiring similar functions are implemented using the same circuitry.

Referring to FIG. 1B which shows a detailed implementation of memory 150 of FIG. 1A, the address of the memory is determined from scan coordinate information in conjunction with the incoming video signal entering on line 102. The data relating to feature intercept locations enters online 102 and is written into memory 101 under control of the address logic 103 responding to scan coordinate signals 104. The memory device may be a random access memory, shift registers, a synchronous disc, a charge couple device memory or an image storage tube.

During the initial scan, data is presented on line 106 through switch 107, while on subsequent scans switch 107 connects to memory output line 108. Switching is caused by controller 161 of FIG. 1A herein. The memory 101, on the subsequent field scans, is in the read mode due to controller 160A and the memory output 109, in conjunction with data from address logic 103 through line 110, form in the output logic 112 a signal essentially identical to the input signal 102 on the previous field scans.

FIG. 2A illustrates an alternate system for implementing either the Reference Area Technique or Reference Slice Technique as referred to in the Summary of Invention. For this configuration it is not necessary to store the entire intercept signal or video signal entering on line 102 as was performed in the entire field memory system of FIG. 1A. The same data, as in FIG. 1A, is used on line 102 and from it, in a manner similar to that already discussed, the intercept logic and coordinate circuit 251 receives the information and generates on line 253, information relating to the X coordinates of specific points within the field of view. This coordinate information is passed to memory 254 where it is stored during an initial field of scan of the specimen under analysis. The X and Y coordinates are derived from line 155, as previously discussed, and are strobed when the intercept logic and coordinate circuit 251 determines a specific point based on the information on line 102. On a subsequent measurement field of scan, the memory 254 outputs data along line 256 into comparator 257 which compares the X coordinate data received on line 155 with the data on line 256 and outputs an index pulse on line 258 when equality occurs between the coordinate data of line 155 and coordinate data on line 256. Simultaneously, on line 260, the video signal enters measurement logic circuit 261 which may be implemented as described in the beforementioned concurrently filed applications with particular reference to concurrently filed application, now U.S. Pat. No. 4,115,806, entitled Image Analysis Data Transfer at, for example, FIGS. 1A and 4B thereof.

The signal on line 260 is a video signal or binary video signal related to the boundaries of the features. It may, in fact, be identical to the data on line 102 depending on the specific measurement to be performed. Alternatively, it may represent the boundaries of features having a different gray value than the boundaries of features which may enter on line 102 or it may represent a true video signal on line 260, whereas the signal on line 1012 may identify the boundaries of features depending on the specific measurement to be performed. In concurrently filed patent application entitled, Image Analysis Data Transfer, the processing of such signals using various configurations of measurement logic circuits is described in detail with particular reference, for example, to FIGS. 4A and 4B thereof.

Because the data entering on line 260 will arise from a different field of scan than the data originating, from an initial field of scan entering on line 102 and resulting in index coordinate data being stored in memory 254, variations in synchronism or alignment will occur between the occurrence of the index points stored as X and Y coordinate information in memory 254 and the data in line 260. Thus, data appearing at the output of measurement logic 261 on line 262 as represented by a pulse on line 312, will be required to be identified to the specific coordinate point stored in memory 254. The alignment logic 265 performing this identification, may be implemented one of two ways.

The first implementation, termed the Reference Area Technique, is for the data coming from the measurement logic 262, during a measurement field of scan, to be positioned by an index pulse on line 258 if it lies within a rectangular reference area of the field of scan. The alignment logic 265 then passes the data out on line 270 with address information on line 272 relating to the index pulse on line 258 in its vicinity.

Figure 2B:
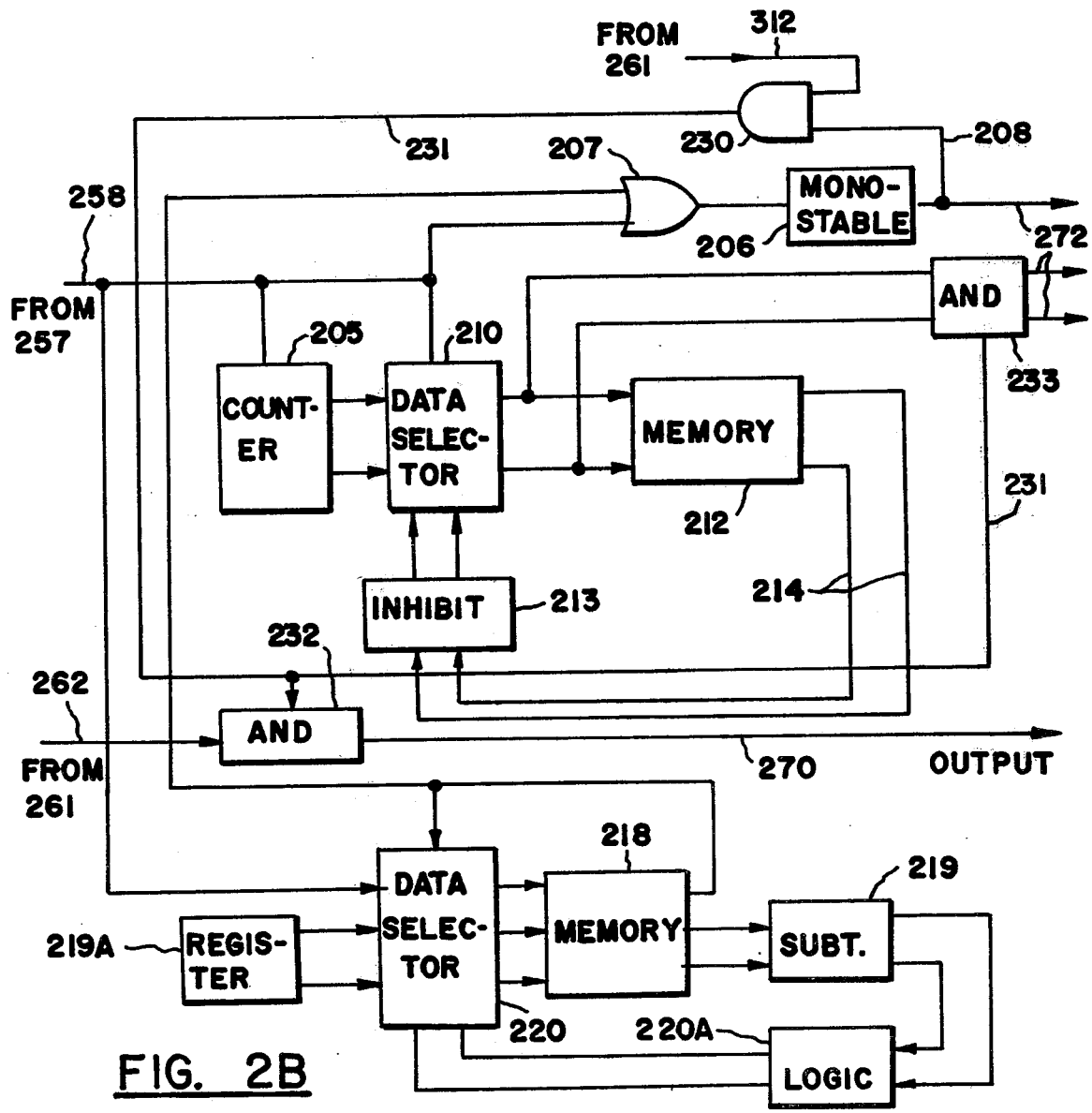
FIG. 2B illustrates data aligning means of FIG. 2A.

This first identification technique termed the Reference Area Technique, relating to the index pulse occurring on line 258, will now be described in detail with respect to FIG. 2B. The index pulse is released, on line 258 from the comparator 257 of FIG. 2A and is passed to counter 205 of FIG. 2B to increment the counter 205. Counter 205 is reset at the beginning of each field of scan. Thus, the counter 205 outputs data corresponding to the number of pulses generated at any given instant from the beginning of the field of scan. Simultaneously, monostable 206 receives the index pulse on line 258 from comparator 257 through OR gate 207 to produce a pulse on line 208 defining the reference area associated with the index pulse. This area may fall along a single scan line, but, in general, it is desirable to identify an index area subtending a number of lines. This is achieved by causing the output of counter 205 to pass into and through data selector 210 into a line-to-line memory 212 to be then stored in inhibitor 213.

Thus, the count number is circulated and appears on the output of memory 212 on lines 214 during the time the index area is intercepted. The duration or X dimension of the index area is defined by monostable 206 being triggered through OR gate 207 from an identifying pulse circulating as one bit in line to line memory 218. The identifying pulse is loaded initially into the line to line memory 218 when the index pulse on line 258 occurs. The total height of the area or Y dimension of the identifying area is defined by loading the number of lines the area is to subtend from register 219A through recirculating data selector 220 into line to line memory 218 and thus into a subtractor 219 which reduces by one the count of the number of lines remaining in the index area. Logic circuit 220A senses the occurrence of a zero count being reached and inhibits the circulating operation through data selectors 220 and 210 thereby completing the index area. Alternatively, the circulation of data in line-to-line memories 212 and 218 for a specific index area may be terminated by inhibit gate 213 and data selector 220 once the condition for data transfer has been satisfied.

Once the index area for a specific point, signaled on line 258, has been identified on line 208, it undergoes an AND operation in AND gate 230 with the signal on line 312 from the measuring logic 261 indicating the occurrence of data on line 262 from the measuring logic 261 as illustrated in FIG. 2A. The resulting signal on line 231 permits multiple AND gate 232 to be open to allow the data on lines 262 from the measuring logic 261 of FIG. 2A to pass to the output of the alignment logic on line 270. Simultaneously, multiple AND gate 233 receives a signal from line 231 which opens AND gate 233 to pass the contents of data selector register 210, identifying the specific index area and hence the specific index point, on line 272 simultaneously with the measurement signal passing on line 270 from the measurement logic. Consequently, the data from the measurement logic 261 passes out on line 270 simultaneously with data on line 272 indicating the number of the index pulse which had occurred on line 258 from comparator 257 and numbered from the beginning of the measurement field of scan which initiated the index area thereby identifying the data from the measurement logic 261. Consequently, the data of measurement logic 261 is identified with the index pulse from comparator 257 through line 258 and, therefore, with the X and Y coordinates stored in memory 254.

FIG. 2C shows a field of view 290 in which an index point 291, displaced an amount related to the size of the reference area by presetting the X and Y coordinates on line 155 during the measurement field of scan to be different from the preset value in the initial field of scan, as discussed in copending application entitled Image Analysis Data Transfer, causes the generation of a reference area 292 occurring across scan lines. Presetting the X and Y coordinates is discussed relative to FIG. 1A and controller 130 of the copending application, now U.S. Pat. No. 4,115,806, entitled Image Analysis Data Transfer. When a measurement data transfer occurs on line 262 at point 293, output data passes on line 270 simultaneously with the transfer of the index point number on line 272. The dotted lines 294 of FIG. 2C show the extent of the reference area if the transfer at point 293 had not occurred.

Figure 3:
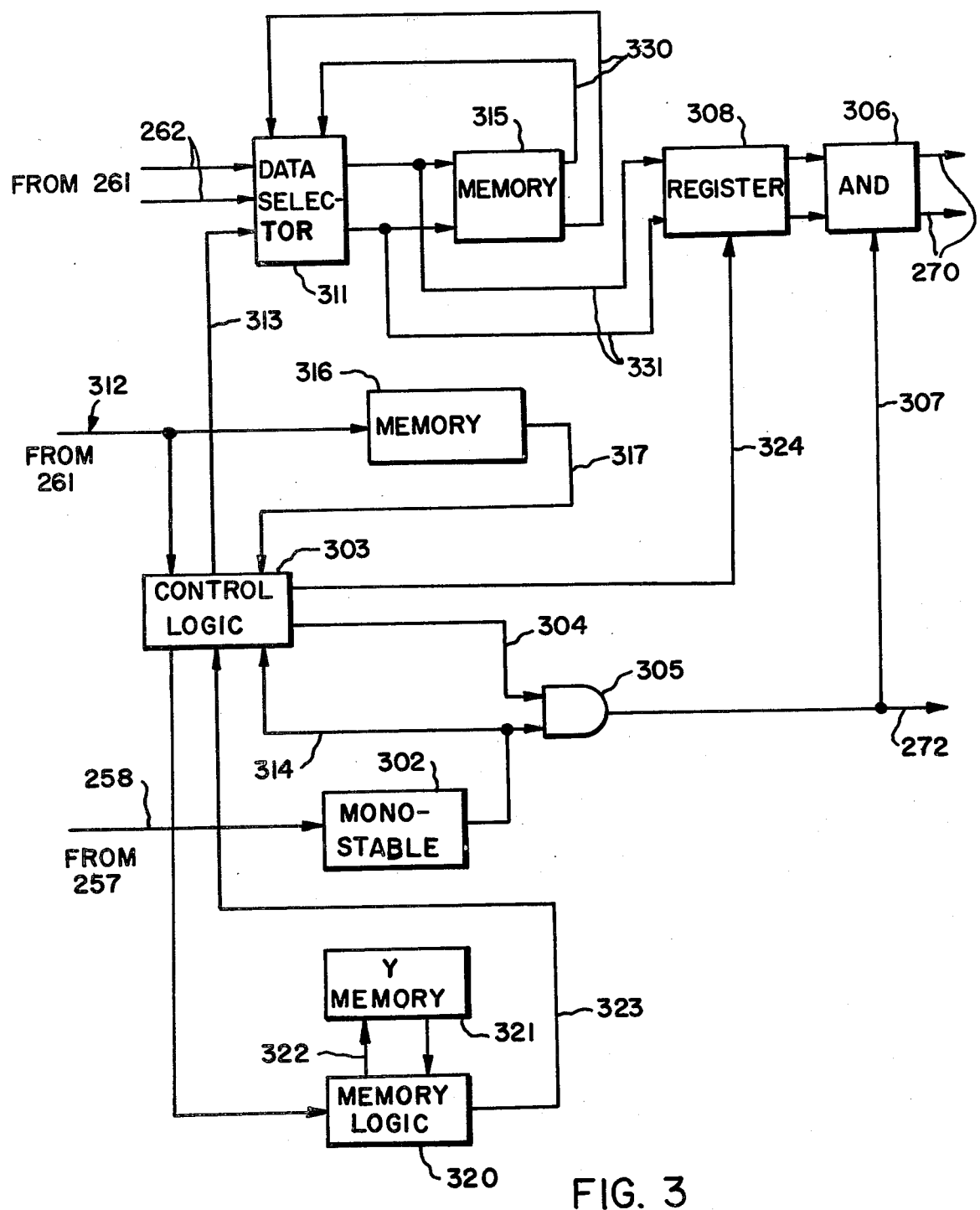
FIG. 3 illustrates an alternate alignment means of FIG. 2A.

The alternate or second implementation identification system referred to as the Reference Slice Technique is shown in FIG. 3. This technique also achieves alignment between data on line 262 of FIG. 2A and the pulse occurring from comparator 258, to thereby identify the X and Y coordinates associated on a previous field with the data arriving at line 262. This alternative technique employs the same overall circuit configuration as shown in FIG. 2A, but provides an alternative implementation for the alignment logic 265 of FIG. 2A.

The index pulse, indicating equality between the X and Y coordinates of the scan and the stored X and Y coordinates, enters on line 258 from comparator 257 of FIG. 2A to monostable 302 which produces an output pulse for a predetermined duration in response to the index pulse. This pulse goes to control logic 303 through line 314 which detects if data is currently available for transfer. If the data is currently available, the control logic 303 sends an enabling signal on line 304 to AND gate 305 and on to multiple AND gate 306 along line 307 to transfer the data resident in register 308 to output lines 270. The data resident in a register 308, had been loaded through lines 331, with data from the current scan line from data outputs on the measurement logic 261 on lines 262, or from memory 315 on lines 330, passing through the data selector 311 to the input of register 308.

Line 312 from measurement logic 261 produces a pulse whenever data is available on lines 262 and this data passes to the control circuitry 303 to control the data selector 311 through line 313 and to load register 308 through line 324. When data is available on lines 262 as signaled by a pulse on line 312, without the concurrence of a signal from monostable 302 to the control logic 303 through line 314, then the control logic 303 causes the data to be loaded through data selector 311, to the memory 315 which stores the data until it is to be read from memory 315 back to data selector 311 to be passed to register 308, controlled through line 324.

The time at which reading operation of memory 315 occurs is determined by line to line memory 316 which stores the X coordinate of the pulse on line 312. At a time when the controller 303 senses that a stored X coordinate signal from the line 317 is coincident with the output of monostable 302 through the line 314, the logic 303 causes data to be released from memory 315 through lines 330 to data selector 311 to register 308, at which time multiple AND gates 306 under control of the signal of line 307, transfers the data to output lines 270, thereby producing at the output lines 270, as a result of index pulse on line 258, the data delayed in memory 315 or in a register 308. A signal on line 272 indicates that data is present on lines 270.

FIG. 2D shows an example of this operation on a field of scan 280. With respect to FIGS. 2A and 3, data is transferred from measurement logic 261 on line 262 at point 281 and is stored in the memory 315 during the time the scan is traversing down the field of view. An index pulse occurs at point 282 and monostable 302 outputs a pulse on line 314 represented by line segment 283. At point 284 the transfer occurs from data in memory 315 to line 270 and a pulse occurs on line 272.

The controller 303 also loads information relating to the Y coordinate of the pulse from line 312 which information is passed by controller 303 into Y memory logic 320 from when it loaded into Y memory 321 through lines 322. Periodically, on a line-by-line basis, the contents of memory 321 is examined to determine the number of lines since the pulse from line 312 occurred. If this number exceeds a predetermined value, then a control signal is sent from the Y control logic 320 through line 323 to cause controller 303 to erase the corresponding entry in memory 315 and memory 316. This ensures that data entered into the memory which is not to be transferred, is not accumulated in the memory indefinitely.

Figure 4:
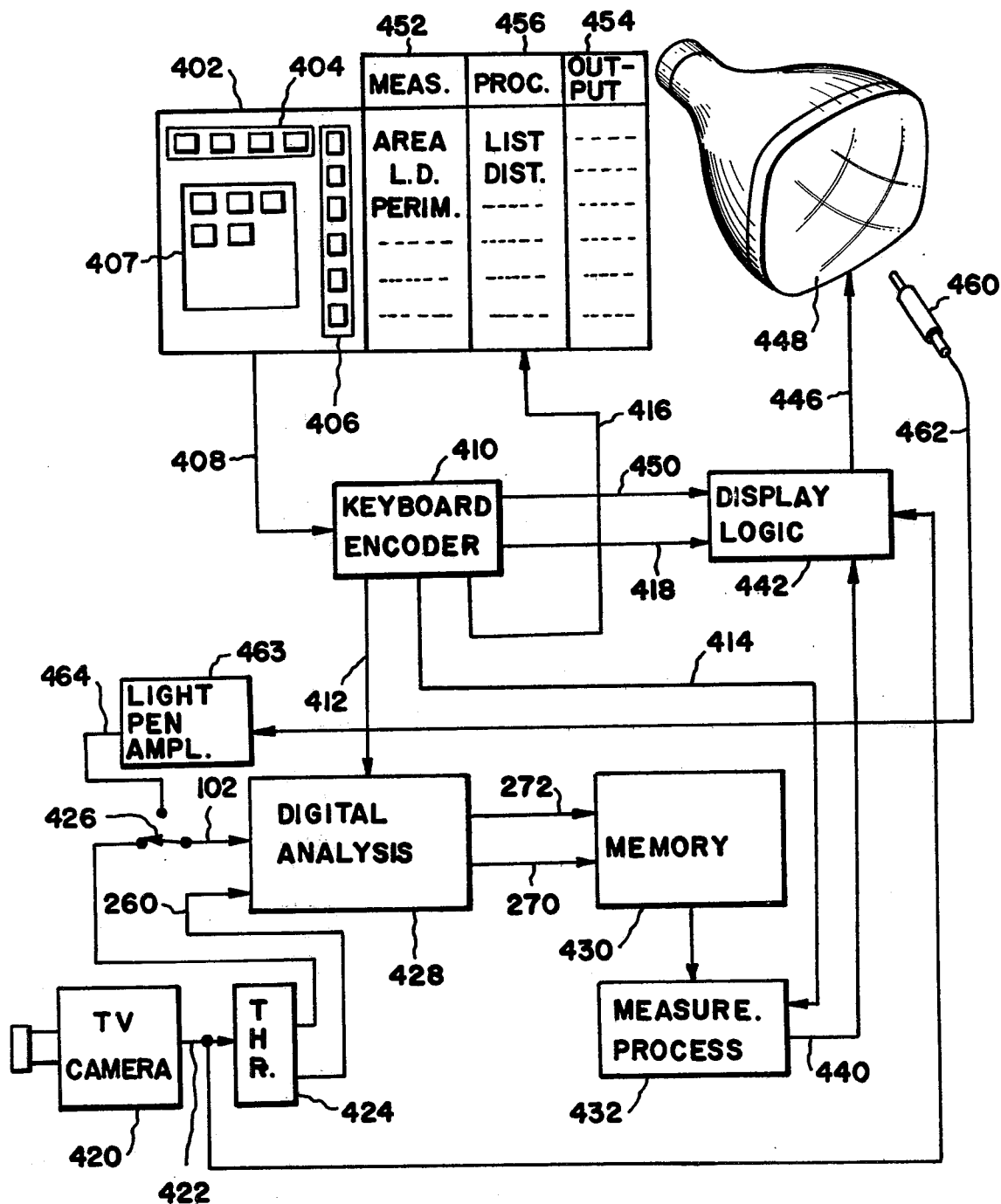
FIG. 4 illustrates communications between an image analysis keyboard status matrix and C.R.T. display.

FIG. 4 illustrates the control and communications aspect of this invention. The special purpose keyboard 402 comprises a number of keys grouped according to their function. Trigger keys are stationed in grouping 404, functional keys are stationed in grouping 406 and additional control keys are stationed in grouping 407. Operation of the keys by the operator generates signals on line 408 to keyboard encoder logic 410 which generates control signals to various portions of the apparatus through lines 412, 414, 416 and 418.

The apparatus includes a television camera 420, generating a video signal on line 422 to a thresholding circuit 424 which passes, via switch 426, data on line 102 which corresponds to line 102 of FIG. 2A. Also entering the digital analysis block 428, corresponding to the apparatus shown in FIG. 2A, is line 260 from threshold circuit 424 corresponding to a video signal or binary video signal depending on the specific measurement.

Data signals, corresponding to lines 272 and 270 containing measurement data extracted in response to the signal on line 260 by the digital analysis block 428, pass to memory 430 where they are stored. Measurement processing logic 432 reads the measurements in memory 430 and performs calculations to derive compound measurements on a per feature basis as explained in copending patent applications entitled, Image Analysis Data Transfer, now U.S. Pat. No. 4,115,806, for example, with reference to FIG. 4A, at FIGS. 1B and 1D of Image Analysis Indexing Apparatus and Methods, now U.S. Pat. No. 4,115,805, and Image at FIGS. 2 and 6B of Analysis Measurement Apparatus and Methods, now U.S. Pat. No. 4,115,803, which data is outputted on line 440 to the display logic 442. In addition, the measurement processing logic 432, depending on the control signals from keyboard encoder 410 through line 414, may accumulate groups of measurements in memory 430 or determine the average of measurement groups in memory 430 or count the number of measurements in memory 430. Measurement processing logic 432 also stores data corresponding to calibration factors for different magnifications between the object being scanned and the image or the object on the face of the T.V. camera 420. These calibration factors are selected by control signals from keyboard 402 and are used by measurement processing logic 432 to ensure that the measurements outputted on line 440 are calibrated in appropriate physical units by multiplying the measurements from memory 430 by the selected calibration factors.

It will be appreciated that other operations may be performed by measurement processing logic 432 on the measurements appearing in memory 430. Some of these operations have been described in the copending application entitled, Image Analysis Indexing Apparatus and Methods, now U.S. Pat. No. 4,115,805, at, for example, FIG. 1D however, others such as statistical processing of the measurements, extraction or size distributions and so on will be familiar to those acquainted with the art.

Display logic 442 combines the video signal from television camera 420 on line 422 with generated signals corresponding to alphanumeric characters. These signals are combined to produce a video signal, on line 446. The video signal on line 446 causes a composite display of the image, as well as alphanumeric data representing measurement results and keyboard operations to be presented on display 448.

The display logic 442 receives from keyboard encoder 410 via line 418, signals corresponding to the keystrokes by the operator on keyboard 402 and character-related signals also appear on line 440 from measurement processing logic 432. These signals are stored in the display logic and processed using state-of-the-art techniques such as are employed, for example, in CAR-MEL Electronics, Inc. M-500 Series Data Traps from CAR-MEL Electronics, Inc., 2218 Cotner Avenue, Los Angeles, California to produce a video signal corresponding to the characters to be displayed. The video signal corresponding to the characters is combined with a video signal representing the image scanned from television camera 420 on line 422 to produce in display logic 442 the video of both image scanned and characters on line 446. In addition, further signals can be combined with the video signal as described in U.S. Pat. No. 3,805,028 at FIG. 37 and discussed in section XV, Column 49 of that reference. Control lines signals from keyboard encoder 410 on line 450 may be used to select the specific signals on line 446 corresponding to images to be displayed on display 448.

The keyboard 402 comprises specially marked keys to relate to the control and operation of the apparatus. These keys are stationed in groups; one group being a trigger group 404 comprising individual keys labeled, for example, Specify Measurement. Pressing this Specify Measurement key indicates to the keyboard encoder 410 that keys of the functional group 406 subsequently pressed, will have the significance of measurements. Upon receiving information that the Specify Measurement key was pressed on line 408, keyboard encoder 410 through line 416 illuminates column 452, labeled Measurement, indicating that the functional keys 406 have the meanings entered in the measurement column opposite each key.

A further trigger key of group 404 labeled Specify Processing has a similar effect in that processing column 456 of status matrix 454 becomes illuminated, indicating that each of the keys in the functional group 406 now have the meaning assigned to them by the entries in the processing column 456. Additional keys in the trigger group 404 include a Start key to start the measurement operation, as well as a Specify Selection key, which is used to indicate the subsequent keys pressed after pressing the Specify Selection key and describe the specific qualifying operation to be performed, using the techniques disclosed in copending patent application entitled, Image Analysis Data Transfer, now U.S. Pat. No. 4,115,806, specifically with respect to FIGS. 1A, 1B, 4A and 4B.

An Enter key included in the control group 407 when pressed, causes any column lit on the status matrix to be extinguished by keyboard encoder 410.

Functional keys in group 406 are aligned in a vertical column, parallel to columns 452 and 456 of status matrix 454. Whenever a functional key of group 406 is pressed after the Specify Measurement key in trigger group 404 is pressed, keyboard encoder logic 410 generates control signals on line 412 to controller 161 of FIG. 1A, included in the digital analysis functional block 428 of FIG. 4. These control signals on line 412 indicate to controller 161 the specific group of control line sequences which controller 161 must execute, thereby implementing the desired measurement. Controller 161 stores groups of control line sequences to control the lines which, as shown in the beforementioned concurrently filed applications, particularly for controller 130 of U.S. Pat. No. 4,115,806, entitled Image Analysis Data Transfer, control the intercept logic 251 or 152, memory 254 and measurement logic 261. Furthermore, in the case of a measurement logic, as set forth herein and as was discussed in copending application entitled, Image Analysis Indexing Apparatus and Methods, now U.S. Pat. No. 4,115,805, wherein the controller 264 in FIG. 1D thereof determined the specific measurement, control signals are passed from keyboard 402 to encoder 410 to the controller of the measurement logic to select a specific sequence of events which are to be performed to implement the specific measurement.

In a similar manner, when the key termed Specify Processing in the trigger group 404 of keyboard 402 of FIG. 4 is pressed, keyboard encoder 410 generates control signals through line 414 which are received by measurement processing logic 432 to execute specific predetermined processing operations on the data in memory 430 and output the results therefrom through line 440 to pass onto display 448.

Light pen 460 may be aligned by the operator to the display 448 in the same manner as was described in U.S. Pat. No. 3,805,028 with specific reference to section II beginning at Column 19. The light pen photosensor in the tip of the pen 460 generates an electrical pulse on line 462 in response to the scanning spot on display 460 passing beneath it. This pulse passes through line 462 to light pen amplifier 463 and by placing switch 426 so that line 102 is connected to 464, it is possible, during an initial field of scan, to define index points along a line defined by the light pen. These index points may be used to extract data from an image along a specific line or as discussed at the Summary Of The Invention in copending application entitled, Image Analysis Data Transfer on index points generated on a line which may on a subsequent field of scan be used to generate a binary signal with transitions at the index points to modify the video signal entering the measurement logic function.

An alternative use of the light pen was disclosed in concurrently filed patent application, Image Analysis Data Transfer, now U.S. Pat. No. 4,115,806, with respect to FIG. 1B. This provided for using the light pen signals on line 464 from light pen amplifier 463 to qualify index points by means of a qualifying transfer.

It will also be appreciated that the signal pulse corresponding to the position of the light pen appearing on line 462 may be implemented by other means, for example, by using a joystick comprising two potentiometers connected in an orthogonal manner to be adjusted by a single lever to generate a voltage on each potentiometer corresponding to the X and Y coordinate. Comparison means receive these voltages and generate a pulse on line 462 when the X and Y coordinates of the scanning spot corresponds to the X and Y coordinate specified by the voltages on the potentiometers.

It is claimed:

1. An image analysis system for extracting data from an image by scanning a field of view, comprising:
keyboard control means having keys for controlling the operation of the system by a key sequence of operation whereby when keys, of said keys for controlling, are keyed sequentially, an image analysis data extracting operation, to be carried out by the image analysis system as a function of the keys keyed and the sequence of keying, is prescribed; and display means associated with the keyboard control means for identifying the function of the keyed keys which function is determined by the keys and the sequence.

2. In an image analysis system for providing image data, a control system comprising:

a keyboard having keys for sequential operation including keys for operator selection identified to specific analysis operations, whereby when a predetermined image analysis operation of said operations is to be provided by the image analysis system, specific keys, of said keyboard keys, including at least one of the keys identified to specific analysis operations, are operated sequentially;

means for encoding the operation and sequence of operation identified by the keys of the keyboard; and a controller for directing the operation of the image analysis system as a function of the specific keys operated.

* * * * *

UNITED STATES PATENT AND TRADEMARK OFFICE
CERTIFICATE OF CORRECTION

PATENT NO. : 4,180,831
DATED : December 25, 1979
INVENTOR(S) : Roger R.A. Morton et al It is certified that error appears in the above-identified patent and that said Letters Patent are hereby corrected as shown below:

Col. 7, line 21, delete "1012" and substitute therefor --102--;

Col. 10, line 35, after "and" (first occurrence) delete "Image"; and line 35, after "of" insert --Image--.

*Signed and Sealed this*

*Eighteenth* Day of *March 1980*

[SEAL]

*Attest:*

SIDNEY A. DIAMOND

*Attesting Officer*     *Commissioner of Patents and Trademarks*